United States Patent [19]

Man

[11] Patent Number: Plant 6,216.

[45] Date of Patent: Jul. 5, 1988

[54] DISTINCT VARIETY OF BEGONIA PLANT NAMED PALOMA

[75] Inventor: Jan Man, Lisse, Netherlands

[73] Assignee: Oglevee Associates, Inc., Connellsville, Pa.

[21] Appl. No.: 885,488

[22] Filed: Jul. 14, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new Begonia variety is characterized by its long lasting, highly floriferous white bloom, short and compact plant form, vigorous growth and smooth texture. The new variety has a high tolerance to botrytis and powdery mildew.

1 Drawing Sheet

BACKGROUND OF THE NEW PLANT

The present invention comprises a new and distinct cultivar of *Begonia*×*hiemalis* known by the varietal name Paloma. The new cultivar is a mutation of the *Begonia hiemalis* Rosalie. The new cultivar Paloma differs from Rosalie in respect of its bloom color. The cultivar Paloma has a tonality from a distance of white whereas the cultivar Rosalie has a tonality from a distance of peach to light orange.

The new cultivar was discovered in April, 1983 at Limaplant b.v. in Lisse, Holland; was first asexually reproduced by cuttings at Limaplant b.v. in Lisse, Holland; and has been repeatedly asexually reproduced by cuttings for Oglevee Associates, Inc. in Connellsville, Pa. It has been found to retain its distinctive characteristics through successive propagations.

The new cultivar is generally characterized by its long lasting, highly floriferous white bloom, short and compact plant form, vigorous growth and smooth texture. The new cultivar has a high tolerance to botrytis and powdery mildew.

The new cultivar, when grown in a greenhouse in Connellsville, Pa., has a response time of nine to ten weeks from a well-rooted cutting to a flowering finished plant in a six inch pot (no pinch).

DESCRIPTION OF THE DRAWING

The accompanying drawing illustrates a new cultivar, the color being as nearly true as possible with color illustrations of this type.

DESCRIPTION OF THE NEW PLANT

The following detailed description sets forth the characteristics of the new cultivar. The data which define these characteristics were collected from asexual reproductions carried out for Oglevee Associates, Inc. in Connellsville, Pa. The plant history was taken on ten week plants blossomed under natural light in a greenhouse and grown under temperature conditions of 62° F. at night and 68° F. during the day. The plants were potted in a peat-lite mix and fertilized with a 100 ppm mixture of 15N-0P-15K. Color reading were taken indoors under 200 footcandles of cool white fluorescent tubes. Color references are to the R.H.S. Colour Chart of The Royal Horticultural Society of London, unless noted differently.

Botanical classification: *Begonia*×*hiemalis.*

Flower:

*Fully expanded.*—5–6 cm across.

*Borne.*—Compound dichasium (cyme).

*Stems.*—Peduncles are upright and sturdy; main peduncle 7 mm in diameter; color yellow-green group 145B.

*Form.*—Semi-double to fully double.

*Permanence.*—Long lasting bloom, generally an individual flower will last 2–3 weeks.

Color:

*Tonality from a distance.*—White.

*Front of petals.*—White group 155B.

*Reverse of petals.*—White group 155B.

*Base of petals.*—Yellow-green group 150D.

*Eye (center).*—Yellow group 4D.

*Discoloration.*—None.

Petals:

*Texture.*—Smooth.

*Appearance.*—Satin, matt finish with ripples.

*Arrangement.*—Whirl; spiral-like.

*Persistence.*—Very persistent, easily bruised.

*Fragrance.*—None.

Reproductive organs:

All reproductive organs have modified into petaloids. Anthers, filament, pollen and style could not be observed.

Plant:

*Form.*—Short, compact, close internodes (1–2 cm apart); good self-support strength, good axillary and basal shoot growth.

*Growth.*—Very vigorous.

*Height from soil line.*—20–22 cm in 10 weeks (no pinch).

*Spread.*—32–36 cm in 10 weeks (no pinch).

Foliage:

*Size.*—Average width of 9 cm and average length of 11 cm.

*Quantity.*—Very abundant.

*Shape.*—Ovate tip with oblique base with a slight overlap of the leaf; edge is doubly serrate.

*Top side.*—Leaf color can vary due to position on plant, light levels, age and fertilization range; green group 137A to 137D.

*Underside.*—Green group 138B to 138C; veins raised in palmate arrangement.

*Ribs and veins.*—Smooth on top, raised on lower side, lower side veins only area where tricomes (hairs) appear.

*Rib and vein color.*—Top side: green group 137D; bottom side: yellow-green group 146A.

*Margin.*—None.

*Stipules.*—None.

*Texture.*—Top: smooth, shiny and leathery; bottom: matt finish with raised veins.

I claim:

1. A new and distinct variety of Begonia characterized by its long lasting, highly floriferous white bloom, short and compact plant form, vigorous growth, smooth texture and high tolerance to botrytis and powdery mildew as herein shown and described and parts therefor.

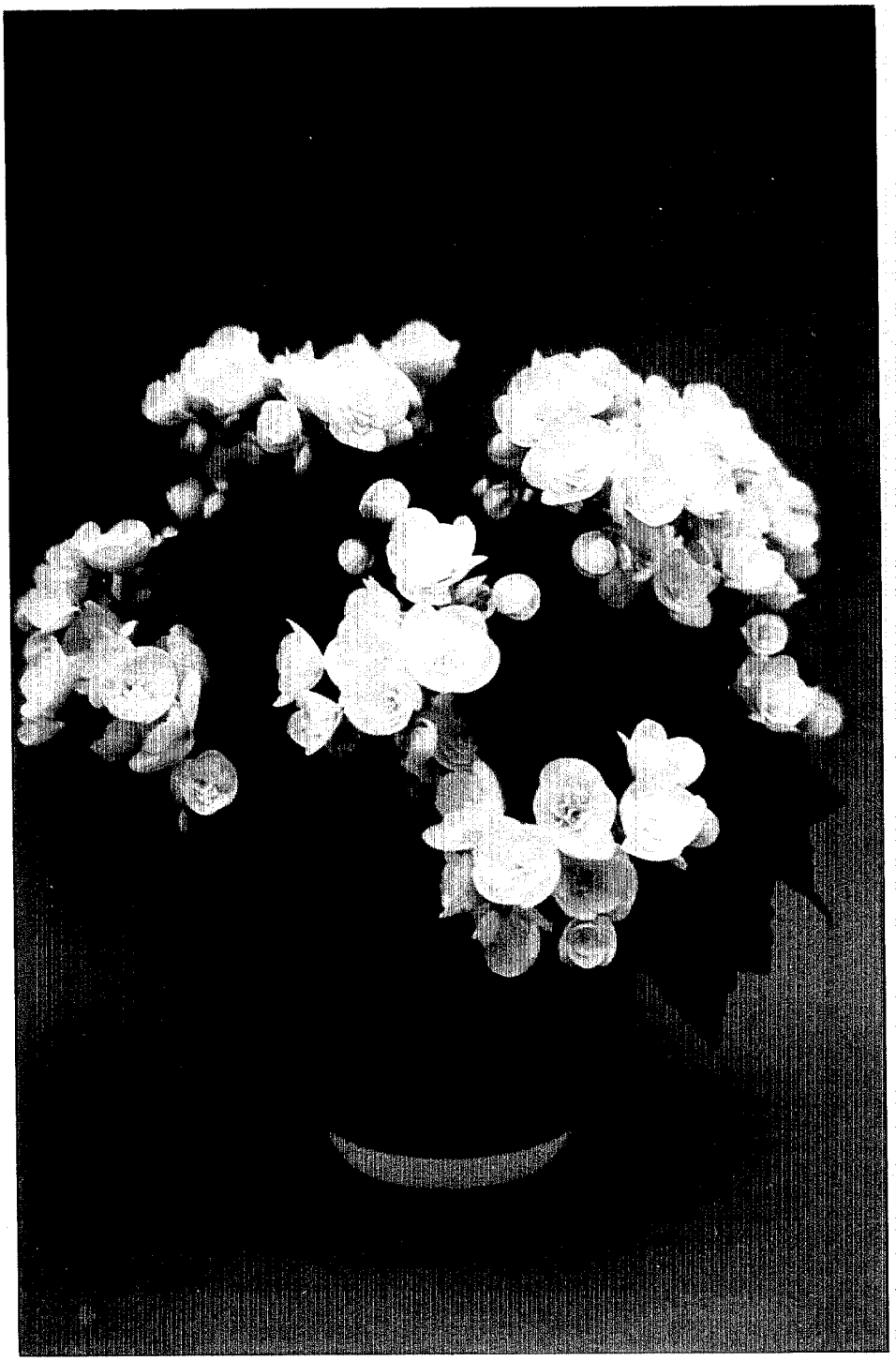

* * * * *